US011333730B2

(12) United States Patent
Saggar

(10) Patent No.: US 11,333,730 B2
(45) Date of Patent: May 17, 2022

(54) SYSTEMS AND METHODS FOR MAPPING NEURONAL CIRCUITRY AND CLINICAL APPLICATIONS THEREOF

(71) Applicant: The Board of Trustees of the Leland Stanford Junior University, Stanford, CA (US)

(72) Inventor: Manish Saggar, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 588 days.

(21) Appl. No.: 16/171,255

(22) Filed: Oct. 25, 2018

(65) Prior Publication Data

US 2019/0120919 A1 Apr. 25, 2019

Related U.S. Application Data

(60) Provisional application No. 62/577,085, filed on Oct. 25, 2017.

(51) Int. Cl.
*G01R 33/48* (2006.01)
*G06T 7/00* (2017.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC . A61B 2576/026; A61B 5/0042; A61B 5/055; A61B 5/16; A61B 5/165;
(Continued)

(56) References Cited

U.S. PATENT DOCUMENTS

2002/0042563 A1* 4/2002 Becerra ............... A61B 5/4064 600/407
2002/0058867 A1* 5/2002 Breiter ................ A61B 5/4064 600/407

(Continued)

FOREIGN PATENT DOCUMENTS

WO 2019084327 A1 5/2019

OTHER PUBLICATIONS

Singh, Gurjeet, Facundo Mémoli, and Gunnar E. Carlsson. "Topological methods for the analysis of high dimensional data sets and 3d object recognition." SPBG 91 (2007): 100. (Year: 2007).*

(Continued)

*Primary Examiner* — Avinash Yentrapati
(74) *Attorney, Agent, or Firm* — KPPB LLP

(57) ABSTRACT

Systems and methods for mapping neuronal circuitry in accordance with embodiments of the invention are illustrated. One embodiment includes a method for generating a neuronal shape graph, including obtaining functional brain imaging data from an imaging device, where the functional brain imaging data includes a time-series of voxels describing neuronal activation over time in a patient's brain, lowering the dimensionality of the functional brain imaging data to a set of points, where each point represents the brain state at a particular time in the timeseries, binning the points into a plurality of bins, clustering the binned points, and generating a shape graph from the clustered points, where nodes in the shape graph represent a brain state and edges between the nodes represent transitions between brain states.

20 Claims, 12 Drawing Sheets
(10 of 12 Drawing Sheet(s) Filed in Color)

(51) Int. Cl.

| | |
|---|---|
| *G06T 7/50* | (2017.01) |
| *A61B 5/00* | (2006.01) |
| *G06K 9/62* | (2022.01) |
| *A61B 5/16* | (2006.01) |
| *G01R 33/56* | (2006.01) |
| *A61B 5/055* | (2006.01) |
| *A61B 5/369* | (2021.01) |

(52) U.S. Cl.
CPC ............... *A61B 5/16* (2013.01); *A61B 5/165* (2013.01); *G01R 33/5608* (2013.01); *G06K 9/6224* (2013.01); *G06K 9/6297* (2013.01); *G06T 7/0012* (2013.01); *G06T 7/50* (2017.01); *A61B 5/369* (2021.01); *A61B 5/4064* (2013.01); *A61B 5/7264* (2013.01); *A61B 5/743* (2013.01); *A61B 2576/026* (2013.01); *G06T 2207/10088* (2013.01); *G06T 2207/30016* (2013.01)

(58) Field of Classification Search
CPC ..... A61B 5/369; A61B 5/4064; A61B 5/7264; A61B 5/743; G01R 33/4806; G01R 33/5608; G06K 9/6224; G06K 9/6297; G06T 2207/10088; G06T 2207/30016; G06T 7/0012; G06T 7/50; G16H 30/40
See application file for complete search history.

(56) References Cited

U.S. PATENT DOCUMENTS

2013/0113816 A1* 5/2013 Sudarsky .............. G06T 11/206
345/589
2016/0350389 A1* 12/2016 Kloke ................. G06F 16/9024

OTHER PUBLICATIONS

Kyeong, Sunghyon, et al. "A new approach to investigate the association between brain functional connectivity and disease characteristics of attention-deficit/hyperactivity disorder: Topological neuroimaging data analysis." PloS one 10.9 (2015): e0137296. (Year: 2015).*

International Search Report and Written Opinion for International Application No. PCT/US2018/057595, Search completed Dec. 11, 2018, dated Dec. 31, 2018, 23 Pgs.

The Virtual Brain, Retrieved from: https://www.thevirtualbrain.org, Printed Jan. 25, 2019, 1 pg.

Abdi et al., "Metric Multidimensional Scaling (MDS): Analyzing Distance Matrices", In Neil Salkind (Ed.) Encyclopedia of Measurement and Statistics (2007), 13 pgs.

Allen et al., "Tracking Whole-Brain Connectivity Dynamics in the Resting State", Cerebral Cortex, vol. 24, No. 3, Mar. 1, 2014, Electronic Publication: Nov. 11, 2012, pp. 663-676.

Barch et al., "Function in the human connectome: Task-fMRI and individual differences in behavior", NeuroImage, 2013, vol. 80, pp. 169-189.

Bassett et al., "Task-Based Core-Periphery Organization of Human Brain Dynamics", PLoS Computational Biology, vol. 9, No. 9, Sep. 26, 2013, e1003171, 16 pgs.

Behzadi et al., "A component based noise correction method (CompCor) for BOLD and perfusion based fMRI", NeuroImage, vol. 37, No. 1, Aug. 1, 2007, Electronic Publication: May 3, 2007, pp. 90-101.

Berman et al., "Depression, rumination and the default network", Social Cognitive and Affective Neuroscience, vol. 6, No. 5, Oct. 2011, Electronic Publication: Sep. 19, 2010, pp. 548-555.

Borgatti et al., "Models of core/periphery structures", Social Networks, vol. 21, No. 4, 1999, pp. 375-395.

Bullmore et al., "Complex brain networks: graph theoretical analysis of structural and functional systems", Reviews, Mar. 2009, vol. 10, pp. 186-198.

Carlsson, "Topological pattern recognition for point cloud data", Acta Numerica, vol. 23, May 12, 2014, pp. 289-368.

Chang et al., "EEG correlates of time-varying BOLD functional connectivity", NeuroImage, vol. 72, May 15, 2013, Electronic Publication: Jan. 31, 2013, pp. 227-236.

Chang et al., "Time-frequency dynamics of resting-state brain connectivity measured with fMRI", NeuroImage, vol. 50, No. 1, Mar. 2010, pp. 81-98.

Cohen, "The behavioral and cognitive relevance of time-varying, dynamic changes in functional connectivity", NeuroImage, vol. 180, Part B, Oct. 15, 2018, pp. 515-525.

Cole et al., "Multi-task connectivity reveals flexible hubs for adaptive task control", Nature Neuroscience, vol. 16, 2013, pp. 1348-1355.

Cole et al., "Prefrontal Dynamics Underlying Rapid Instructed Task Learning Reverse with Practice", The Journal of Neuroscience, vol. 30, No. 42, Oct. 20, 2010, pp. 14245-14254.

Cribben et al., "Dynamic connectivity regression: Determining state-related changes in brain connectivity", NeuroImage, vol. 61, No. 4, Jul. 16, 2012, pp. 907-920.

Cunningham et al., "Dimensionality reduction for large-scale neural recordings", Nature Neuroscience, vol. 17, Aug. 24, 2014, pp. 1500-1509.

Damaraju et al., "Dynamic functional connectivity analysis reveals transient states of dysconnectivity in schizophrenia", NeuroImage: Clinical, vol. 5, Jul. 24, 2014, pp. 298-308.

Damoiseaux et al., "Consistent resting-state networks across healthy subjects", PNAS, Sep. 12, 2006, vol. 103, No. 37, pp. 13848-13853.

Demirtas et al., "Dynamic Functional Connectivity Reveals Altered Variability in Functional Connectivity Among Patients With Major Depressive Disorder", Human Brain Mapping, vol. 37, No. 8, Apr. 28, 2016, pp. 2918-2930.

Fortunato, "Community detection in graphs", Physics Reports, vol. 486, No. 3-5, Feb. 2010, pp. 75-174.

Glasser et al., "The Human Connectome Project's neuroimaging approach", Nature Neuroscience, vol. 19, Aug. 26, 2016, pp. 1175-1187.

Glasser et al., "The minimal preprocessing pipelines for the Human Connectome Project", NeuroImage, 2013, available online May 11, 2013, vol. 80, pp. 105-124.

Gonzalez-Castillo et al., "Task-based dynamic functional connectivity: Recent findings and open questions", NeuroImage, vol. 180, Part B, Oct. 15, 2018, pp. 526-533.

Gonzalez-Castillo et al., "Tracking ongoing cognition in individuals using brief, whole-brain functional connectivity patterns", Proceedings of the National Academy of Sciences, vol. 112, No. 28, Jul. 14, 2015, pp. 8762-8767.

Grabner et al., "Symmetric Atlasing and Model Based Segmentation: An Application to the Hippocampus in Older Adults", International Conference on Medical Image Computing and Computer-Assisted Intervention, LNCS, vol. 4191, MICCAI 2006, pp. 58-66.

Handwerker et al., "Periodic changes in fMRI connectivity", NeuroImage, vol. 63, No. 3, Nov. 15, 2012, pp. 1712-1719.

Hinton et al., "Stochastic Neighbor Embedding", Proceedings of the 15th International Conference on Neural Information Processing Systems, 2002, pp. 857-864.

Hutchison et al., "Dynamic functional connectivity: Promise, issues, and interpretations", NeuroImage, vol. 80, Oct. 15, 2013, pp. 360-378.

Hutchison et al., "Resting-State Networks Show Dynamic Functional Connectivity in Awake Humans and Anesthetized Macaques", Human Brain Mapping, vol. 34, No. 9, Sep. 2013, pp. 2154-2177.

Jia et al., "Behavioral Relevance of the Dynamics of the Functional Brain Connectome", Brain Connectivity, vol. 4, No. 9, Nov. 1, 2014, pp. 741-759.

Keilholz et al., "Dynamic Properties of Functional Connectivity in the Rodent", Brain Connectivity, vol. 3, No. 1, Feb. 19, 2013, Online Publication: Jan. 29, 2013, pp. 31-40.

(56) References Cited

OTHER PUBLICATIONS

Killick et al., "Optimal Detection of Changepoints With a Linear Computational Cost", Journal of the American Statistical Association, vol. 107, No. 500, Oct. 17, 2012, pp. 1590-1598.

Klein et al., "Evaluation of volume based and surface-based brain image registration methods", NeuroImage, vol. 51, No. 1, May 15, 2010, pp. 214-220.

Lindquist et al., "Evaluating dynamic bivariate correlations in resting-state fMRI: A comparison study and a new approach", NeuroImage, vol. 101, Nov. 1, 2014, Online Publication: Jun. 30, 2014, pp. 531-546.

Liu et al., "Time-varying functional network information extracted from brief instances of spontaneous brain activity", Proceedings of the National Academy of Sciences, vol. 110, No. 11, Mar. 12, 2013, pp. 4392-4397.

Lum et al., "Extracting insights from the shape of complex data using topology", Scientific Reports, vol. 3, No. 1236, Feb. 7, 2013, 8 pgs.

Mill et al., "From connectome to cognition: The search for mechanism in human functional brain networks", NeuroImage, vol. 160, Oct. 15, 2017, pp. 124-139.

Newman, "Fast algorithm for detecting community structure in networks", Physical Review E, vol. 69, No. 6, Jun. 18, 2004, 066133, 5 pgs.

Nicolau et al., "Topology based data analysis identifies a subgroup of breast cancers with a unique mutational profile and excellent survival", Proceedings of the National Academy of Sciences, vol. 108, No. 17, Apr. 26, 2011, pp. 7265-7270.

Petridou et al., "Periods of Rest in fMRI Contain Individual Spontaneous Events which are Related to Slowly Fluctuating Spontaneous Activity", Human Brain Mapping, vol. 34, No. 6, Jun. 2013, pp. 1319-1329.

Ponce-Alvarez et al., "Task-Driven Activity Reduces the Cortical Activity Space of the Brain: Experiment and Whole-Brain Modeling", PLoS Computational Biology, vol. 11, No. 8, Aug. 28, 2015, e1004445, 26 pgs.

Power et al., "Functional Network Organization of the Human Brain", Neuron, Nov. 17, 2011, vol. 72, pp. 665-678.

Preti et al., "The dynamic functional connectome: State-of-the-art and perspectives", NeuroImage, vol. 160, Oct. 15, 2017, pp. 41-54.

Prichard et al., "Generating Surrogate Data for Time Series with Several Simultaneously Measured Variables", Physical Review Letters, vol. 73, No. 7, Aug. 15, 1994, pp. 951-954.

Rashid et al., "Dynamic connectivity states estimated from resting fMRI Identify differences among Schizophrenia, bipolar disorder, and healthy control subjects", Frontiers in Human Neuroscience, vol. 8, No. 897, Nov. 7, 2014, 13 pgs.

Ravizza et al., "The impact of context processing deficits on task-switching performance in schizophrenia", Schizophrenia Research, vol. 116, No. 2-3, Feb. 2010, pp. 274-279.

Romano et al., "Topological Methods Reveal High and Low Functioning Neuro-Phenotypes Within Fragile X Syndrome", Human Brain Mapping, vol. 35, No. 9, Sep. 2014, pp. 4904-4915.

Rombach et al., "Core-Periphery Structure in Networks", SIAM Journal on Applied Mathematics, vol. 74, No. 1, Feb. 18, 2014, pp. 167-190.

Roweis et al., "Nonlinear Dimensionality Reduction by Locally Linear Embedding", Science, vol. 290, Dec. 22, 2000, pp. 2323-2326.

Saggar, "Quantifying fluctuations in intrinsic brain activity using topology", Stanford University School of Medicine, Center for Interdisciplinary Brain Sciences Research (CIBSR), Presentation, Mar. 8, 2016, 7 pgs.

Saggar, "Saggar_Supplementary Movie M1", Vimeo, Jul. 11, 2017, Retrieved from: https://vimeo.com/225062058/ae65e20aaa, 2 pgs.

Saggar et al., "(only) time will tell: revealing the shape of brain dynamics during ongoing cognition", Presentation slide, Psychiatry and Behavioral Sciences, Stanford University School of Medicine, Oct. 12, 2016, 1 pg.

Saggar et al., "Towards a new approach to reveal dynamical organization of the brain using topological data analysis", Entire document. Nature Communications 9, Article No. 1399 (2018). pp. 14, Published—Apr. 11, 2018.

Shine et al., "Estimation of dynamic functional connectivity using Multiplication of Temporal Derivatives", NeuroImage, vol. 122, Nov. 15, 2015, pp. 399-407.

Shine et al., "Temporal metastates are associated with differential patterns of time-resolved connectivity, network topology, and attention", Proceedings of the National Academy of Sciences, vol. 113, No. 35, Aug. 30, 2016, pp. 9888-9891.

Shine et al., "The Dynamics of Functional Brain Networks: Integrated Network States during Cognitive Task Performance", Neuron, vol. 92, No. 2, Oct. 19, 2016, pp. 544-554.

Singh et al., "Topological analysis of population activity in visual cortex", Journal of Vision, vol. 8, No. 8, Jun. 30, 2008, 18 pgs.

Singh et al., "Topological Methods for the Analysis of High Dimensional Data Sets and 3D Object Recognition", Eurographics Symposium on Point-Based Graphics, 2007, 11 pgs.

Smith, "The future of FMRI connectivity", NeuroImage, vol. 62, No. 2, Aug. 15, 2012, pp. 1257-1266.

Smith et al., "Correspondence of the brain's functional architecture during activation and rest", Proceedings of the National Academy of Science, vol. 106, No. 31, Aug. 4, 2009, pp. 13040-13045.

Smith et al., "Resting-state fMRI in the Human Connectome Project", NeuroImage, vol. 80, Oct. 15, 2013, pp. 144-168.

Smith et al., "Temporally-independent functional modes of spontaneous brain activity", Proceedings of the National Academy of Science, vol. 109, No. 8, Feb. 21, 2012, pp. 3131-3136.

Sourty et al., "Identifying Dynamic Functional Connectivity Changes in Dementia with Lewy Bodies Based on Product Hidden Markov Models", Frontiers in Computational Neuroscience, vol. 10, No. 60, Jun. 23, 2016, 11 pgs.

Sporns, "Making sense of brain network data", Nature Methods, vol. 10, No. 6, Jun. 2013, pp. 491-493.

Sporns, "Network attributes for segregation and integration in the human brain", Current Opinion in Neurobiology, vol. 23, No. 2, Apr. 2013, pp. 162-171.

Tagliazucchi et al., "Dynamic BOLD functional connectivity in humans and its electrophysiological correlates", Frontiers in Human Neuroscience, vol. 6, No. 339, Dec. 28, 2012, 22 pgs.

Tenenbaum et al., "A Global Geometric Framework for Nonlinear Dimensionality Reduction", Science, vol. 290, No. 5500, Dec. 22, 2000, pp. 2319-2323.

Ugurbil et al., "Pushing spatial and temporal resolution for functional and diffusion MRI in the Human Connectome Project", NeuroImage, vol. 80, Oct. 15, 2013, pp. 80-104.

Van Der Maaten et al., "Visualizing Data using t-SNE", Journal of Machine Learning Research, vol. 9, Nov. 2008, pp. 2579-2605.

Welvaert et al., "neuRosim: An R Package for Generating fMRI Data", Journal of Statistical Software, vol. 44, No. 10, Oct. 2011, 18 pgs.

Woodcock et al., "Neural correlates of task switching in paternal 15q11-q13 deletion Prader-Willi syndrome", Brain Research, vol. 1363, Dec. 6, 2010, pp. 128-142.

Woolrich et al., "Mixture Models With Adaptive Spatial Regularization for Segmentation With an Application to FMRI Data", IEEE Transactions on Medical Imaging, vol. 24, No. 1, Jan. 1, 2005, 11 pgs.

Xu et al., "Dynamic connectivity detection: an algorithm for determining functional connectivity change points in fMRI data", Frontiers in Neurosciences, vol. 9, No. 285, Sep. 4, 2015, 19 pgs.

Yao et al., "Topological methods for exploring low-density states in biomolecular folding pathways", The Journal of Chemical Physics, vol. 130, No. 14, Apr. 14, 2009, 11 pgs.

Yarkoni et al., "Large-scale automated synthesis of human functional neuroimaging data", Nature Methods, Aug. 2011, vol. 8, No. 8, 10 pgs., published online Jun. 26, 2011.

Zalesky et al., "Time-resolved resting-state brain networks", Proceedings of the National Academy of Science, vol. 111, No. 28, Jul. 15, 2014, pp. 10341-10346.

(56) References Cited

OTHER PUBLICATIONS

International Preliminary Report on Patentability for International Application PCT/US2018/057595, Report dated Apr. 28, 2020, dated May 7, 2020, 8 Pgs.
Welcome to C-PAC's Documentation, Retrieved from: htttps://web.archive.org/web/20160503042759/http://fcp-indi.github.io/docs/user/index.html, C-PAC 0.3.9 Alpha, Captured May 3, 2016.

* cited by examiner

- Instructions
- Resting State
- Working Memory
- Video
- Math

● Instructions
● Resting State
● Working Memory
● Video
● Math

● Instructions
● Resting State
● Working Memory
● Video
● Math

- Instructions
- Resting State
- Working Memory
- Video
- Math

SYSTEMS AND METHODS FOR MAPPING NEURONAL CIRCUITRY AND CLINICAL APPLICATIONS THEREOF

CROSS-REFERENCE TO RELATED APPLICATIONS

The current application claims the benefit of and priority under 35 U.S.C. § 119(e) to U.S. Provisional Patent Application No. 62/577,085 entitled "Towards a new approach to visualize and quantify brain's dynamical organization using topological analysis" filed Oct. 25, 2017. The disclosure of U.S. Provisional Patent Application No. 62/577,085 is hereby incorporated by reference in its entirety for all purposes.

STATEMENT OF FEDERALLY SPONSORED RESEARCH

This invention was made with Government support under contract MH104605 awarded by the National Institutes of Health. The Government has certain rights in the invention.

FIELD OF THE INVENTION

The present invention generally relates to the mapping of neuronal circuitry and, more specifically, to the generation and application of neuronal shape graphs.

BACKGROUND

The human brain is the central organ of the human nervous system, and with the spinal cord makes up the central nervous system. The brain consists of the cerebrum, the brainstem and the cerebellum. It controls most of the activities of the body, processing, integrating, and coordinating the information it receives from the sense organs, and making decisions as to the instructions sent to the rest of the body. The cerebrum is the largest part of the human brain. It is divided into two cerebral hemispheres. Each hemisphere is conventionally divided into four lobes—the frontal, temporal, parietal, and occipital lobes. The frontal lobe is associated with executive functions including self-control, planning, reasoning, and abstract thought, while the occipital lobe is dedicated to vision. Within each lobe, cortical areas are associated with specific functions, such as the sensory, motor and association regions. Although the left and right hemispheres are broadly similar in shape and function, some functions are associated with one side, such as language in the left and visual-spatial ability in the right. The hemispheres are connected by commissural nerve tracts, the largest being the corpus callosum.

The cells of the brain include neurons and supportive glial cells. There are more than 86 billion neurons in the brain, and a more or less equal number of other cells. Brain activity is made possible by the interconnections of neurons and their release of neurotransmitters in response to nerve impulses. Neurons connect to form neuronal pathways, neuronal circuits, and elaborate network systems. The whole circuitry is driven by the process of neurotransmission.

SUMMARY OF THE INVENTION

Systems and methods for fabricating a metal core truss panel with seamlessly embedded features in accordance with embodiments of the invention are illustrated. One embodiment includes a method for generating a neuronal shape graph, including obtaining functional brain imaging data from an imaging device, where the functional brain imaging data includes a time-series of voxels describing neuronal activation over time in a patient's brain, lowering the dimensionality of the functional brain imaging data to a set of points, where each point represents the brain state at a particular time in the time-series, binning the points into a plurality of bins, clustering the binned points, and generating a shape graph from the clustered points, where nodes in the shape graph represent a brain state and edges between the nodes represent transitions between brain states.

In another embodiment, lowering the dimensionality of the functional brain imaging data is performed using a neighborhood lens function.

In a further embodiment, binning the points partitions the low dimensional points into overlapping bins.

In still another embodiment, clustering the binned points is achieved using single-linkage clustering.

In a still further embodiment, the imaging device is a functional magnetic resonance imaging machine.

In yet another embodiment again, the neuronal mapping application further directs the processor to identify a community structure within the shape graph.

In yet another embodiment, the functional brain imaging data is resting state functional brain imaging data.

In a yet further embodiment, the method further includes generating a Markov chain graph.

In another additional embodiment, the method further includes annotating the nodes in the shape graph with task data.

In a further additional embodiment, the method further includes identifying at least one set of core nodes and at least one set of periphery nodes in the shape graph.

In another embodiment again, the method further includes identifying a community structure within the shape graph.

In a further embodiment again, a system for generating a neuronal shape graph includes at least one processor, and at least one memory, including a neuronal mapping application, where the neuronal mapping application directs the processor to obtain functional brain imaging data from an imaging device, where the functional brain imaging data comprises a time-series of voxels describing neuronal activation over time in a patient's brain, lower the dimensionality of the functional brain imaging data to a set of points, where each point represents the brain state at a particular time in the time-series, bin the points into a plurality of bins, cluster the binned points, and generate a shape graph from the clustered points, where nodes in the shape graph represent a brain state and edges between the nodes represent transitions between brain states.

In still yet another embodiment, the neuronal mapping application further directs the processor to lower the dimensionality of the functional brain imaging data is performed using a neighborhood lens function.

In a still yet further embodiment, the bins are overlapping.

In still another additional embodiment, the neuronal mapping application directs the processor to cluster the binned points using single-linkage clustering.

In a still further additional embodiment, the imaging device is a functional magnetic resonance imaging machine.

In still another embodiment again, the functional brain imaging data is resting state functional brain imaging data.

In a still further embodiment again, the neuronal mapping application further directs the processor to generate a Markov chain graph.

In yet another additional embodiment, the neuronal mapping application further directs the processor to annotate the nodes in the shape graph with task data.

In a yet further additional embodiment, the neuronal mapping application further directs the processor to identify at least one set of core nodes and at least one set of periphery nodes in the shape graph.

In yet another embodiment again, the neuronal mapping application further directs the processor to identify a community structure within the shape graph.

In a still further embodiment again, the imaging device is an electroencephalogram device.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

DETAILED DESCRIPTION

Figure 1:
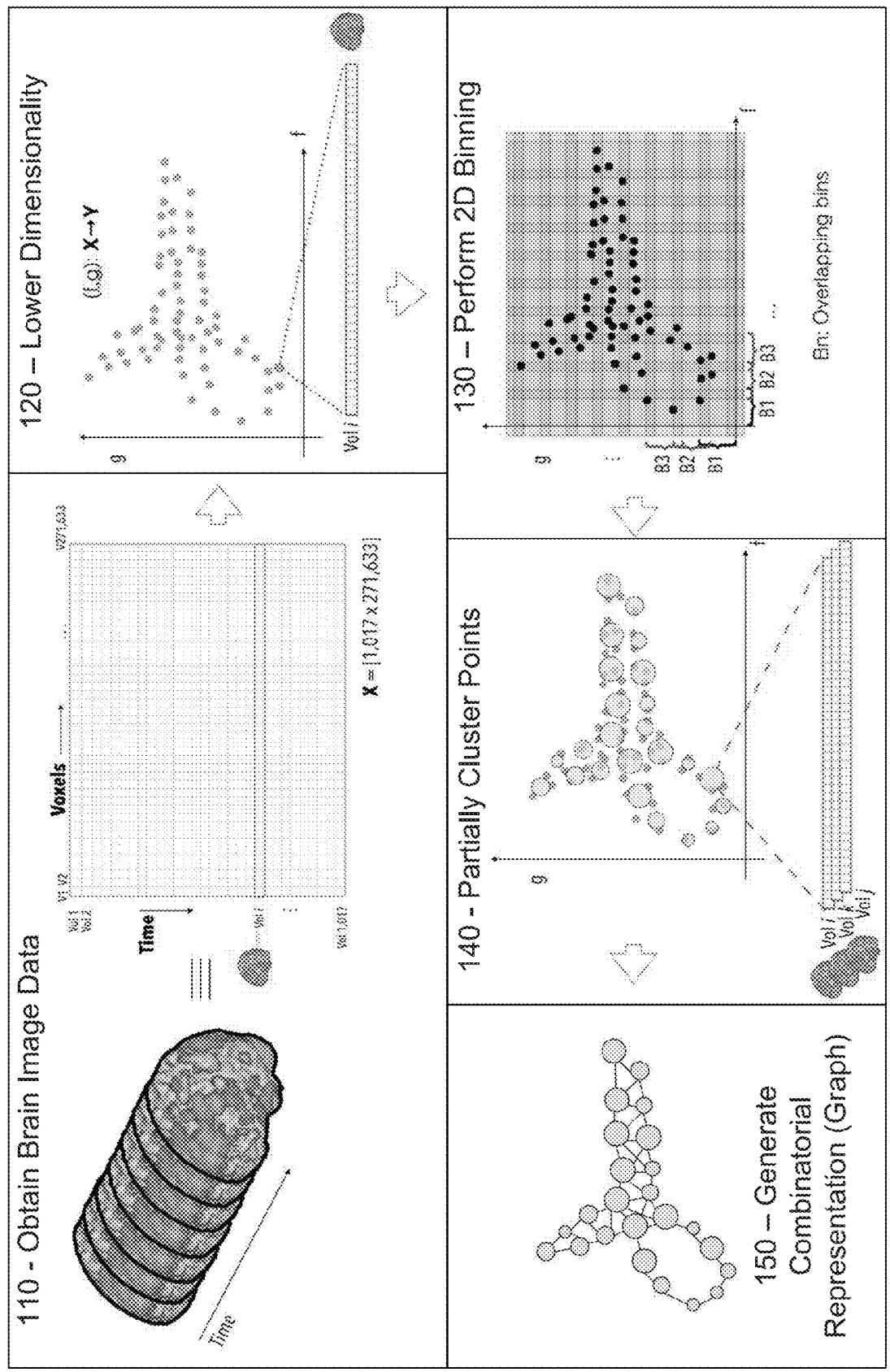
FIG. 1 is a graphical flow chart illustrating a process for generating shape graphs in accordance with an embodiment of the invention.

According to the National Institute of Mental Health, a branch of the Department of Health and Human Services, nearly one in five adults in the United States experiences mental illness in a given year. Traditionally, mental health has been diagnosed based on clusters of behaviors by psychologists and psychiatrists. Indeed, the principal authority for psychiatric diagnoses is the Diagnostic and Statistical Manual of Mental Disorders (DSM-5) which takes this approach of codifying mental disorders by behavior. However, there are numerous conditions which have overlapping behaviors, and it can be difficult to determine a correct diagnosis. This can lead to improper treatment and progression of a mental disorder. In contrast, physical conditions are generally diagnosed by a combination of biological features (i.e. pathophysiology). If biological bases for mental disorders could be reliably identified in a clinical setting, a significant amount of guesswork could be removed from the mental health diagnostic process.

With the development and rise of neuroimaging techniques, medical researchers and clinicians have the ability to non-invasively investigate the biological features of a patient's brain. Specifically, functional brain imaging techniques produce functional brain imaging data that describes neuronal activation in a live brain over time. Despite advances in functional imaging, little is known about how our brain dynamically adapts for efficient functioning. Most previous work has focused on estimating co-fluctuations in the activity extracted from a set of brain regions. The dynamical aspect is then measured by assessing changes in these co-fluctuations over the course of several temporal windows. However, by collapsing data in space (i.e., over brain regions) or time (i.e., over temporal windows), potentially useful information could be lost about the brain's dynamical organization. Indeed, recent studies show that within-subject properties of functional connectivity (FC) can vary considerably not solely across different scans, but also within the confines of individual scans (at the relatively fast timescales of seconds). Studies have suggested that the origin of temporal variations is neurophysiological, and that such variations contain clinically relevant information. Thus, the current understanding of the brain functioning based on "average" FC, and the accompanying inferences, is at best, incomplete.

Presently, several fundamental issues remain unresolved, including—(1) uncovering the temporal and spatial scales that best capture clinically and behaviorally relevant brain dynamics; (2) understanding whether the dynamical landscape of possible configurations is best conceptualized as continuous or discrete; and (3) recognizing what constitutes healthy and aberrant dynamics. Tackling these issues requires novel tools that avoid arbitrarily collapsing data in time and space early in the analysis, provide interpretable visualizations of how the brain traverses its dynamical landscape and permit quantification of these dynamic trajectories in behaviorally and clinically relevant ways that allow comparisons across conditions, subjects and populations. For diagnostic techniques using neuroimaging data to be clinically useful, it is helpful if the technique is robust against noise, can reliably pick up stable, personalized traits, and sensitive enough to capture changes in mental states. In numerous embodiments, systems and methods described herein are robust, reliable, and sensitive.

Systems and methods described herein reveal the overall dynamical organization of whole-brain activity as a combinatorial object (or a graph, referred to herein as "shape graphs") without arbitrarily collapsing data in space or time. For example, in many embodiments, these combinatorial objects, called shape graphs, can be used to predict the performance capabilities of an individual. In a variety of embodiments, shape graphs can be used to uniquely identify ("fingerprint") individuals. In numerous embodiments, shape graphs can be used to identify clinical mental health disorders. Indeed, shape graphs can be used for any of a wide array of clinical applications by providing insight into the neuronal pathways of an individual.

Shape graph representations can be interactively visualized (making them optimal for exploratory research), can be quantified in a variety of ways using graph theory, and can be constructed at the level of individual participants, making them suitable for translational purposes. In many embodiments, Topological Data Analysis (TDA) is used to represent the inherent structure of high-dimensional functional neuroimaging data as a simplicial complex. These representations are analogous to generating a topographical map that can capture the essential features of a landscape.

Shape graphs can encapsulate the original "shape" (i.e., topological and geometric information) of the data. In numerous embodiments, nearby points are more similar than distant points. Intuitively, such a representation can be analogized to generating a topographical map that can capture the essential features of a landscape. Neuronal mapping processes described herein can provide many advantages over traditional manifold learning (or non-linear dimensionality reduction) algorithms (e.g., ISOMAP). For example, in many embodiments, unlike manifold learning, neuronal mapping processes make fewer assumptions about the underlying data. Further, unlike other traditional methods, neuronal mapping processes can represent the landscape as a graph, which is robust to noise and its properties can be easily estimated for better quantification. Additionally, the coordinate and deformation invariance properties of various neuronal mapping processes make them suitable for examining data across participants and projects. Neuronal mapping processes for generating shape graphs are discussed below.

Neuronal Mapping Processes for Generating Shape Graphs

The concept of the connectome, or a map of the connections between different regions of the brain, was proposed within the last decade. In that time, the conventional form of brain mapping has been largely limited to connectograms (for connectional connectivity) and brain atlases (for physical structures). However, the form of a connectogram does not enable a deep understanding of an individual brain's circuit network, or show the paths of activation within a brain. In contrast, the structure of a graph is intuitive for human users, and can provide a deeper understanding of the data through its topology. Neuronal mapping process can be used to convert functional brain imaging data into shape graphs. In many embodiments, neuronal mapping processes can use TDA processes such as, but not limited to, implementations of the MAPPER algorithm (first described in "Topological Methods for the Analysis of High Dimensional Data Sets and 3D Object Recognition" by Singh, Mémoli, and Carlsson of Stanford University) to generate shape graphs. Indeed, while specific processes described herein utilize algorithms similar to the MAPPER algorithm, any number of TDA processes can be used as appropriate to the requirements of a given application. Further, while the systems and methods below are discussed in detail with respect to functional brain imaging data obtained via functional magnetic resonance imaging (fMRI), any number of functional imaging techniques can be used, such as, but not limited to, positron emission tomography (PET) scans, functional near-infrared spectroscopy (fNIRS), electroencephalogram (EEG), and/or any other functional imaging methodology as appropriate to the requirements of specific applications of embodiments of the invention.

Turning now to FIG. 1, a neuronal mapping process for generating a shape graph in accordance with an embodiment of the invention is illustrated. Process 100 includes obtaining (110) functional brain imaging data. In numerous embodiments, functional brain imaging data is a time series of images, where each image in the time series of images reflects the location of neuronal activation in a brain at a given time. In many embodiments, functional brain imaging data is a matrix, where rows correspond to individual time frames, and columns correspond to the voxels, where the value of each cell reflects the intensity of neuronal activation at that voxel at that time. In a variety of embodiments, the time series image data and the matrix are functionally equivalent, either can be derived from the other. In the embodiment, illustrated in FIG. 1, a total of 1,017 time frames were used, and a 3 mm isotropic resolution was utilized for a total of 271,633 voxels. However, one of ordinary skill in the art can appreciate that any length of time frame and imaging resolution could be utilized as appropriate to the requirements of a given application of the invention. Indeed, resolution can be dependent upon the quality of the imaging system utilized, various safety requirements, or any other of a number of testing requirements.

Process 100 further includes reducing (120) the dimensionality of the data. In numerous embodiments, dimensionality is reduced using a filtering process. Intuitively, the filtering step can be thought of as a "lens" through which data is looked at. In a variety of embodiments, the filtering process is similar to the standard dimensionality reduction techniques used in machine learning. However, unlike traditional linear dimensionality reduction techniques, like Principal Component Analysis (PCA) or multi-dimensional scaling (MDS), filtering processes can employ a nonlinear dimensionality reduction method using a variant of Stochastic Neighborhood Estimation (SNE). In a variety of embodiments, geometric filters (e.g., distance-based density, measures of centrality, etc.) and/or non-geometric filters (e.g., derived from PCA or projection pursuit analysis) can be used for the filtering step. In some embodiments, a Neighborhood Lens function is used to project the high-dimensional data (in 271,633 dimensions) to two dimensions (for visualization). The Neighborhood Lens function is a nonlinear dimensionality reduction method that uses a variant of Stochastic Neighborhood Estimation (t-SNE). Nonlinear methods like SNE can allow for preservation of the "local" structure in the original high dimensional space after projection into the low dimensional space. Thus, the time frames (TR, or volumes) with similar activation patterns in the original high dimensional space can be projected closer to each other in the reduced dimensional space.

The graph accompanying step 120 depicts this filtering step, where the time frames that were originally acquired in the high-dimensional space (i.e., 271,633 voxels) are projected to a two-dimensional filter space (represented as (f,g)) using the nonlinear dimensionality reduction method. Note that after filtering, the number of data points is the same as the number of initial time frames (i.e., 1,017 frames for each participant).

Process 100 further includes performing 2D binning. To encapsulate the low-dimensional representation generated by the filtering step, binning (or partitioning) can be employed. In many embodiments, the binning step partitions the low-dimensional space into overlapping bins by using two parameters: number of bins (or resolution (R)) and percentage of overlap between bins (or gain (G)). This approach selected R=30 and G=3. However, the parameters can be modified to compensate for higher or lower sampling rates. Indeed, the parameters are robust to parameter perturbation, and therefore parameters can be tuned to functional brain imaging data used.

The process 100 further includes partially clustering (140) points. Within each bin, partial clustering can be performed to reduce the complexity of the shape graph. The resulting clusters from this step later can become nodes in the shape graph. There is no required particular clustering approach. In many embodiments, a single-linkage clustering algorithm is used, as it does not require specifying the number of clusters beforehand. The distance metric for single-linkage clustering could be chosen to be Euclidean or correlation or any other similarity function. In many embodiments, the distance metric used is the Manhattan L1 metric. However, any number of clustering algorithms can be used with any number of metrics as appropriate to the requirements of a given application of the invention.

Process 100 further includes generating (150) the combinatorial object shape graph. In many embodiments, each cluster is treated as a node in the graph, and each node is connected with an edge if they share one or more data points (or time frames). Shape graphs can be conceptualized as a low-dimensional depiction of how the brain dynamically evolved across different functional configurations during the scan. While the actual interpretation of the latent variables associated with the projected low-dimensional space may differ across subjects, the topological relationships encoded by the shape graph itself can be interpretable and comparable across subjects. Shape graphs as descried are capable of demonstrating functional connectivity in the brain. However, shape graphs can be further leveraged by annotating them with additional data. For example, if the functional brain imaging data was obtained in conjunction with a set of tasks performed by the patient, the shape graph can be annotated with the tasks that correspond at each time frame. If a node contains time frames from multiple tasks, the node can be annotated with the proportion of time frames that belong to each task within the node (e.g. by a pie chart). Once generated, the structure of shape graphs can be analyzed and information extracted. Neuronal mapping processes for quantifying the mesoscale properties of shape graphs are discussed below.

Neuronal Mapping Processes for Quantifying Mesoscale Properties of Shape Graphs

Graph (or network) theory is currently widely used in the field of neuroscience to provide summary statistics of the complex interactions between different entities or nodes. While interesting insights can be captured by analyzing properties of each node or edge in the network (i.e., at the local scale) or by analyzing the network as whole (i.e., at the global scale), the intermediate (or mesoscale) properties appear particularly well suited for analyzing and comparing the structure of complex networks. In particular, considerable effort has gone into identifying two distinct types of mesoscale structures in a variety of complex networks. The first and perhaps the most widely used mesoscale structure is the community structure, where cohesive groups called "communities" consist of nodes that are densely connected to other nodes within communities while being only sparsely connected to nodes between communities. In the context of shape graphs representing brain's dynamical organization, the presence of communities could represent a modular organization with specialized whole-brain functional configurations for different types of information processing (or tasks). An increasingly second most typical mesoscale structure is the core-periphery structure. Here, one attempts to determine the "core" nodes that are not only densely connected to each other but are also "central" to the entire network. A presence of cores in shape graphs representing brain's dynamical organization could indicate whole-brain functional configurations that consistently occur and, in some cases, could also represent neuronal processes that the brain passes through when traveling between other configurations (e.g., neuronal processes related to task-switching during a multitask experimental paradigm). The peripheral nodes are only sparsely connected.

Beginning with community analysis, in many embodiments, to quantify the community structure in a shape graph, a quality function $Q_{mod}$ is estimated. Mathematically, for a given graph G, with N nodes and a set of edges E connecting those nodes, $Q_{mod}$ can be defined as: $Q_{mod}=\Sigma_{\{i,j\}}[A_{ij}-P_{ij}]\delta(g_i, g_j)$, where A is the adjacency matrix, with $A_{ij}$ as cell elements containing the weight of connection between nodes i and j. For a hard partition (i.e., where each node is assigned to exactly one community) and where $g_k$ denotes the community for node k, the function $(g_i, g_j)=1$ if $g_i=g_j$ and equals to 0 otherwise. $P_{ij}$ denotes expected connection strength between nodes i and j, under a specified null model. One of the most common null models is given by: $P_{ij}=k_ik_j/2m$, where $k_i$ is the strength of node i, $k_j$ is the strength of node j, and $m=\frac{1}{2}\Sigma_{ij} A_{ij}$. However, any number of different quality functions can be used as appropriate to the requirements of a given application of the invention. In general, a higher modularity score ($Q_{mod}$) is associated with enhanced performance.

For quantifying core-periphery structure, in many embodiments, a generalized Borgatti and Everett algorithm that provides a "coreness score (CS)" for each node along a continuous spectrum between nodes that lie most deeply in a network core (CS~1) and those that are in the periphery (CS~0). CS can be estimated using an implementation of the Rombach et al. algorithm, which was designed for undirected networks. This can take into account cores of different shapes and sizes by giving credit to all nodes and by weighting the credit using a quality function $R_{(\alpha,\beta)}$, defined: $R_{(\alpha,\beta)}=\Sigma_{ij}A_{ij}C_{ij}$, where $(\alpha,\beta)$ are the two parameters, such that $\beta$ sets the size of the core and $\alpha$ sets the boundary between core and periphery (i.e., large value of $\alpha$ indicates sharp transition). The symbol A denotes the adjacency matrix, with $A_{ij}$ as cell elements containing the weight of connection between nodes i and j. The elements $C_{ij}$ of the core matrix are given by $C_{ij}=C_iC_j$, and $C_i \geq 0$ is the local core value of node i. The local core values of node i, $C_i$, is estimated by maximizing $(\alpha,\beta)$ using Simulated Annealing. The aggregate of coreness score of each node i is, $CS(i)=Z\Sigma_{(\alpha,\beta)}C_i(\alpha,\beta)\times R(\alpha,\beta)$, where Z is a normalization factor such that the CS(i) normalizes to a maximum value of 1.

Figure 2A:
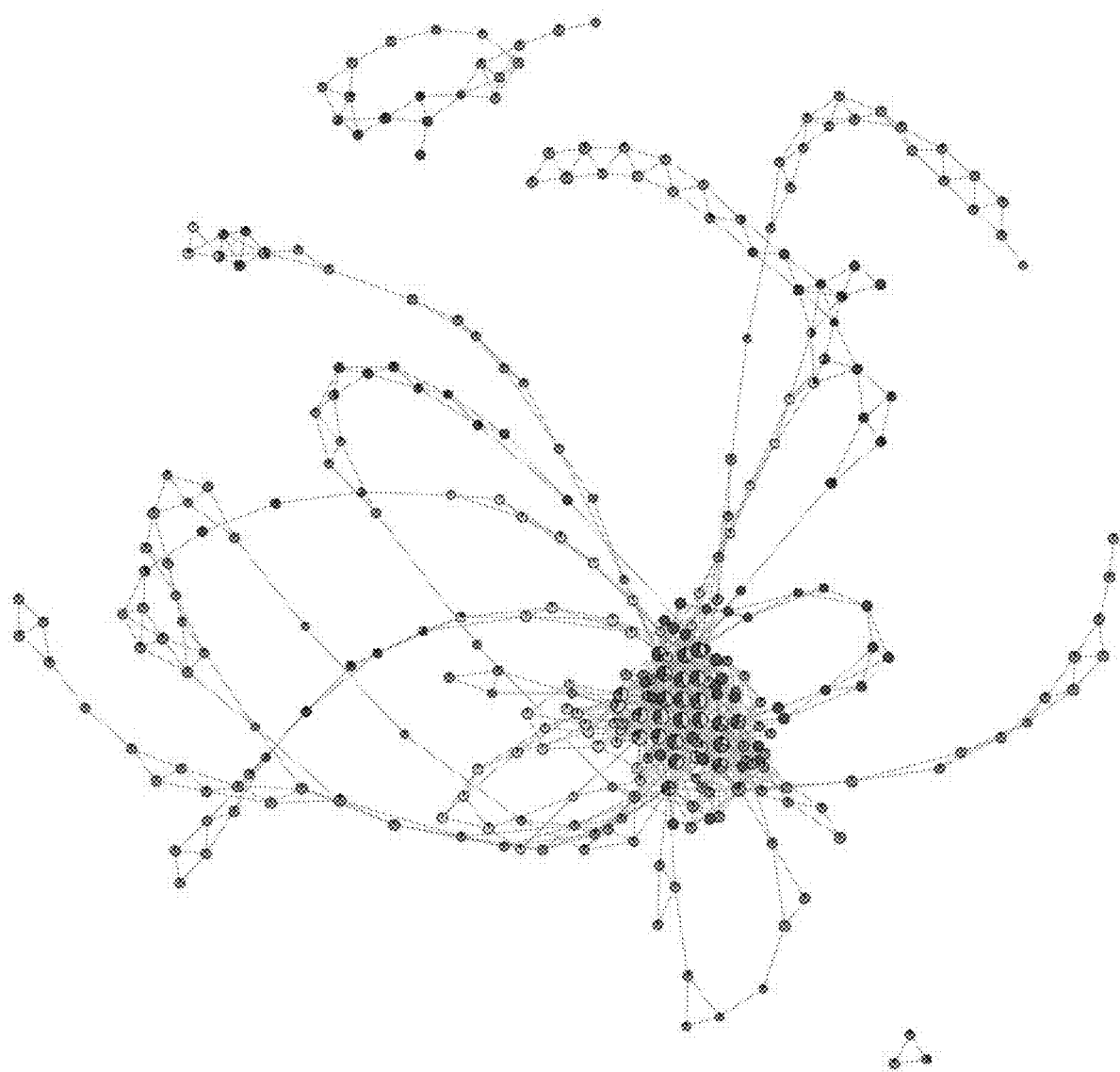
FIG. 2A illustrates a shape graph labeled with task information in accordance with an embodiment of the invention.
Figure 2B:
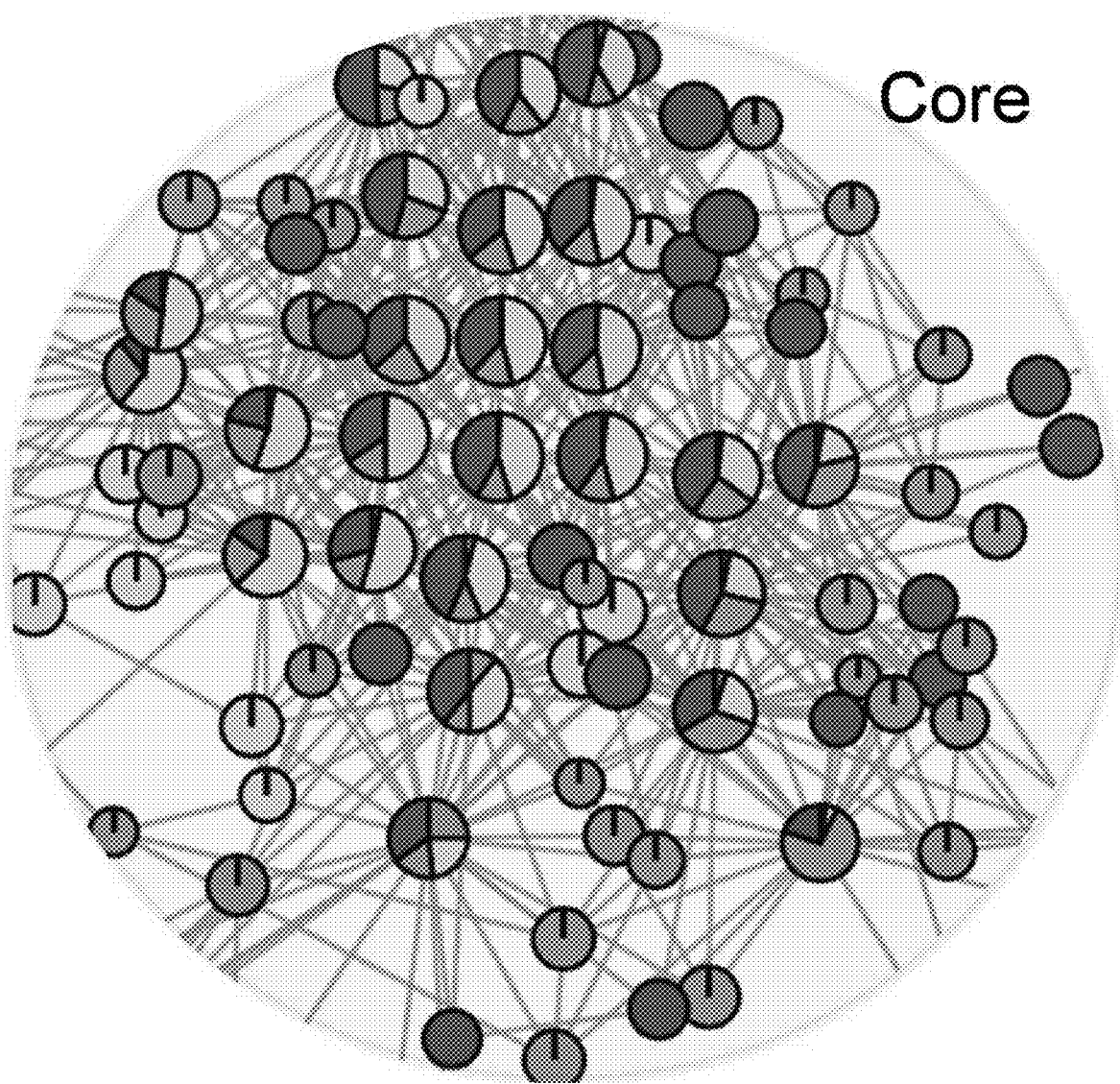
FIG. 2B is a zoomed in view of the core portion of the shape graph of FIG. 2A in accordance with an embodiment of the invention.

The core-periphery structure of a shape graph can give clinical insights into a patient. Shape graphs in accordance with embodiments of the invention are illustrated in FIGS. 2A-2D. Turning now to FIG. 2A, an example shape graph in accordance with an embodiment of the invention is illustrated. The shape graph has been annotated with task data. In this shape graph, multiple circuits that lead outwards from a central cluster (the "core") of the graph can be seen. In numerous embodiments, these periphery structures (here as tendril-like structures) indicate specialized circuitry for particular tasks. In contrast, the core structure represents unspecialized circuitry. A presence of cores in shape graphs representing brain's dynamical organization can indicate whole-brain functional configurations that consistently occur and, in some cases, can also represent neuronal processes that the brain passes through when traveling between other configurations (e.g., neuronal processes related to task-switching during a multitask experimental paradigm). The peripheral nodes are only sparsely connected. Thus, examination of the core-periphery structure could reveal the overall arrangement of the network. The core of the shape graph illustrated in FIG. 2A is illustrated in FIG. 2B.

Figure 2C:
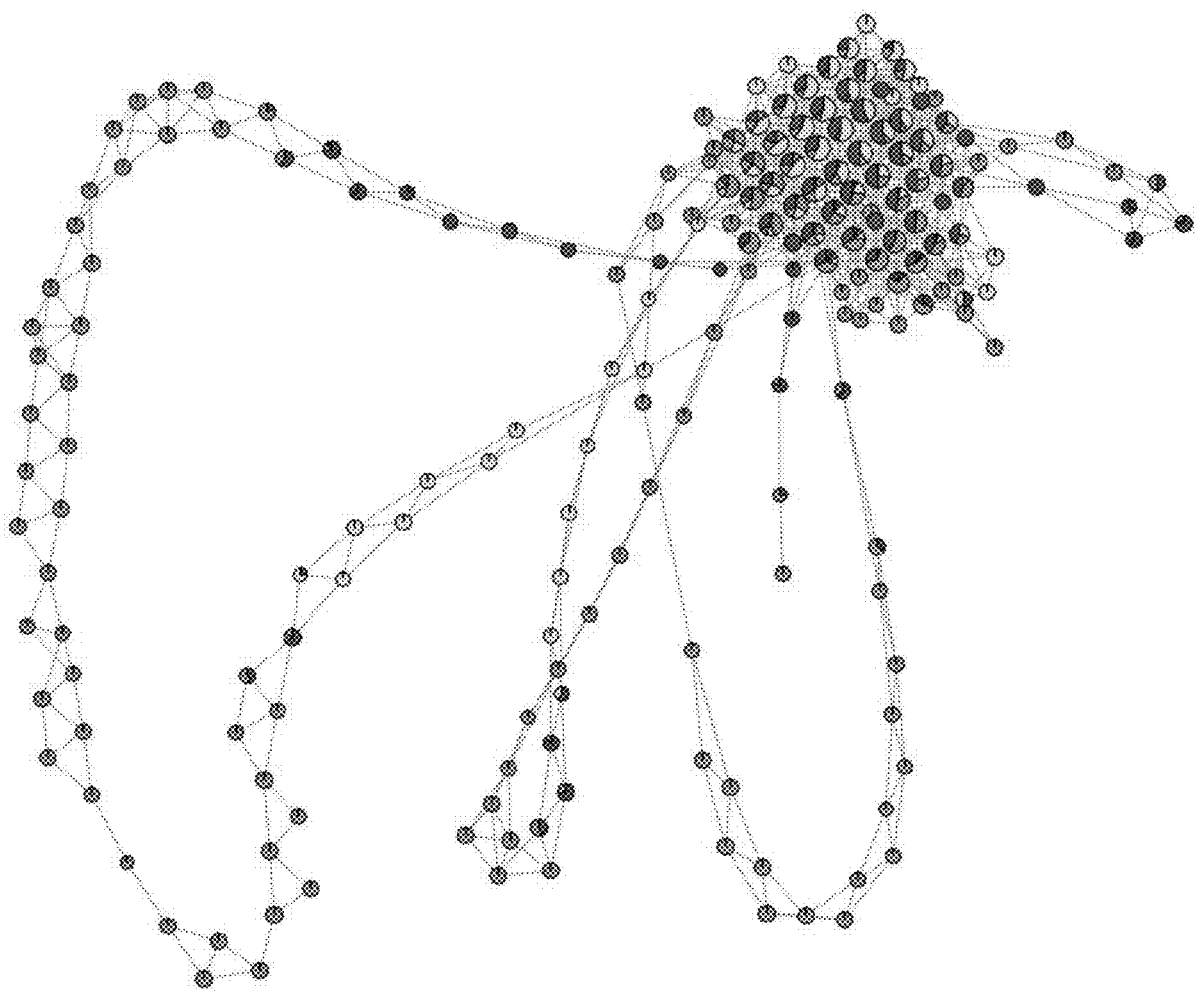
FIG. 2C illustrates the shape graph of a "poor performer" in accordance with an embodiment of the invention.
Figure 2D:
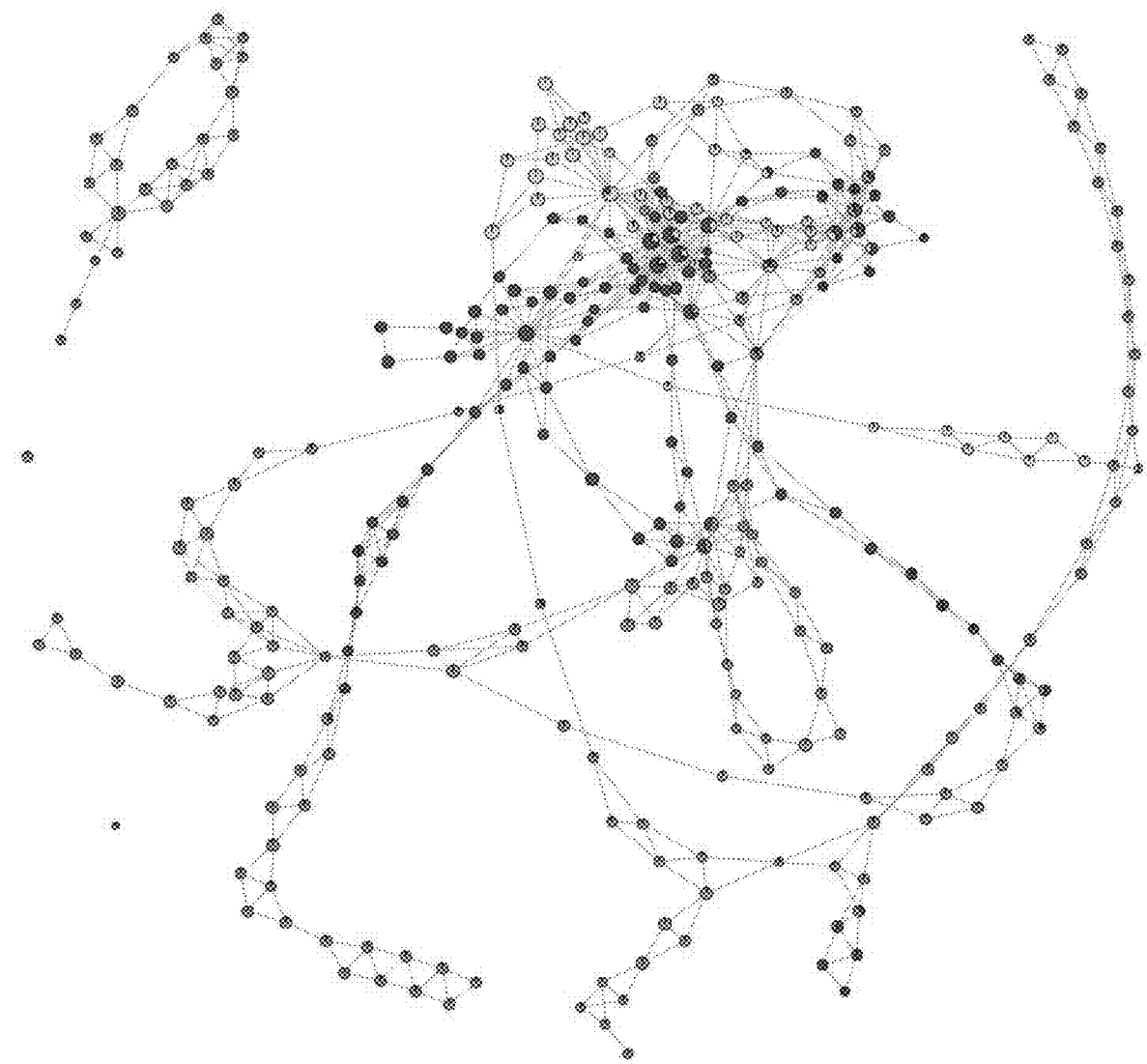
FIG. 2D illustrates the shape graph of a "good performer" in accordance with an embodiment of the invention.

In many embodiments, the presence of multiple, specialized periphery structures are found in "better" performers, i.e. those who score better on tasks associated with the peripheral structures. An exemplary shape graph of a "poor" performer in accordance with an embodiment of the invention is illustrated in FIG. 2C. In contrast, an exemplary shape graph of a "good" performer in accordance with an embodiment of the invention is illustrated in FIG. 2D. The difference in structure in terms of number of peripheral structures is visually evident, demonstrating the intuitive benefits of shape graphs. Further, it can be beneficial to ground insights gained from the overall shape of the graph back to the patient's brain. Neuronal mapping processes for grounding insights are discussed further below.

Neuronal Mapping Processes for Grounding Insights

To ground the shape graphs and their properties into neurophysiology, several methods can be utilized to reveal the underlying patterns of brain activity putatively responsible for the observable topological features. Indeed, neuronal mapping processes can include processes for further annotating and animating shape graphs to demonstrate causal brain activity. In some embodiments, spatial mixture modeling (SMM) can be used to interactively reveal changes in brain activation maps from one time frame to the next. In a variety of embodiments, SMM approaches include fitting a mixture of distributions and using a spatial Markov random field to regularize (smooth) the labeling of voxels into null, activated or de activated. Thus, for each node in the shape graph and the containing time frames, whole-brain activation (and deactivation) maps can be generated. Activation and deactivation maps can be animated. For example, in real time, a user can move a Time-Frame slider (across time frames) to simultaneously highlight respective nodes in a digital representation of the shape graph, see transitions in corresponding whole-brain activation maps, and/or observe correlations of the activation maps with known large-scale brain networks. This can allow inspection of neurophysiology at the whole-brain level and the highest temporal resolution (limited only by acquisition rate).

Figure 3:
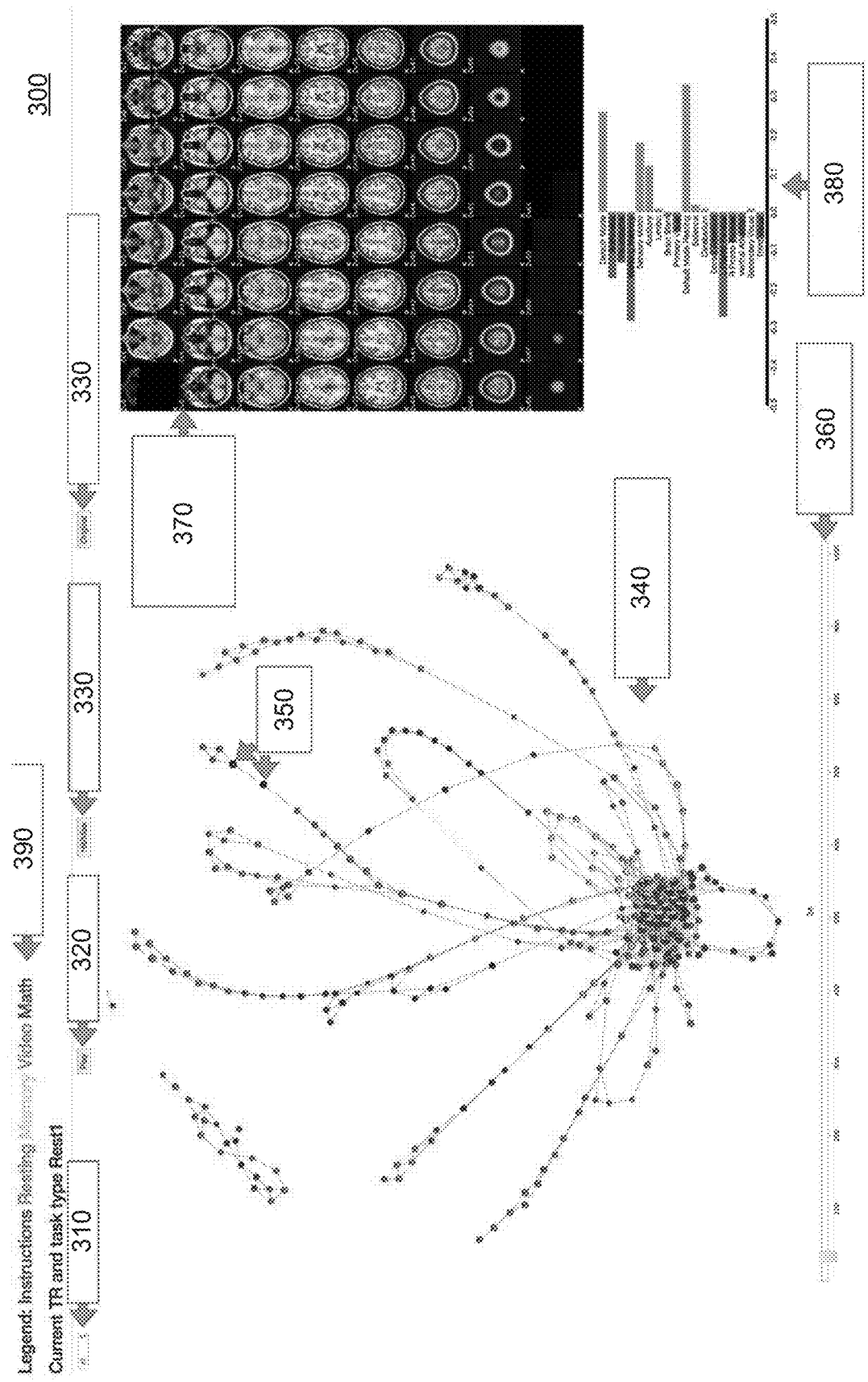
FIG. 3 illustrates a shape graph display in accordance with an embodiment of the invention.

Turning now to FIG. 3, a display for viewing shape graphs in accordance with an embodiment of the invention is illustrated. Display window 300 includes a selection mechanism 310 for selecting participant data to display, a play button 320 to animate the shape graph, and can include a toggle to optionally display hit/miss trials. Display window 300 also includes a button to revert all display parameters to their default values. Display window 300 includes a shape graph 340 corresponding to the participant selected. The shape graph animation can include sequentially highlighting shape graph nodes 350 in the order of activation during testing. The animation can be moved forward or backwards by a user using a time slider 360 by navigating over TRs. An overlay of the spatial profile 370 for each time point can be provided in the display window 300, as well as a dynamic display of correlation with known large-scale brain networks 380. While a specific display configuration in accordance with an embodiment of the invention is illustrated in FIG. 3, any number of configurations can be utilized, including, but not limited to, reducing the amount of information provided, increasing the number of statistics provided, adding additional animation parameters, or any other changes as appropriate to the requirements of a given application of an embodiment of the invention.

Furthermore, in a variety of embodiments, to anchor the overall topological properties of the shape graph into neurophysiology, a traditional group-based generalized linear model (GLM) analysis can be used. Specifically, the neurophysiological basis for the observed non-trivial mesoscale structure of core-periphery in the shape graphs can be observed. For a GLM analysis, the coreness score of each node can be mapped back to the individual time frames contained in that node. Thus, if a node has a CS of 0.5, then the time frames contained in that node also received a CS of 0.5. Using multiple regression, the CS for each time frame can be entered for each task (i.e., four explanatory variables). In many embodiments, contrasts can be run to examine brain regions that show positive as well as negative association with the coreness scores. In various embodiments, for the positive association contrast, during the working memory tasks, higher coreness scores are associated with increased engagement of the bilateral dorsolateral prefrontal cortex (DLPFC), bilateral insula and lateral occipital cortex, and paracingulate gyrus. Higher coreness scores during the math tasks can be associated with increased engagement of the R. angular gyrus, inferior parietal sulcus areas and the paracingulate gyrus. For video tasks, higher coreness scores can be positively associated with activation in the bilateral fusiform gyrus and right frontal pole. Qualitatively, the brain regions associated positively with coreness scores overlap with regions previously shown to be recruited for the respective tasks. For the negative association contrast, across all three tasks, significant clusters can be observed in the posterior cingulate cortex (PCC) and medial prefrontal cortex, as nodes with lower coreness scores (or periphery nodes) can be associated with increased activation in the PCC irrespective of the task type. As such, core nodes in the shape graph can represent task-related activation and putatively associated cognitive effort, whereas sparsely and peripherally connected nodes in the shape graph can represent task-unrelated activation presumably related to task-negative default mode regions.

While two specific methods are discussed above, any number of annotations could be applied to shape graphs as appropriate to the requirements of a given application of the invention. Further, shape graphs, as discussed above with respect to task data, can be further used to explore the transition states between tasks.

Figure 4A:
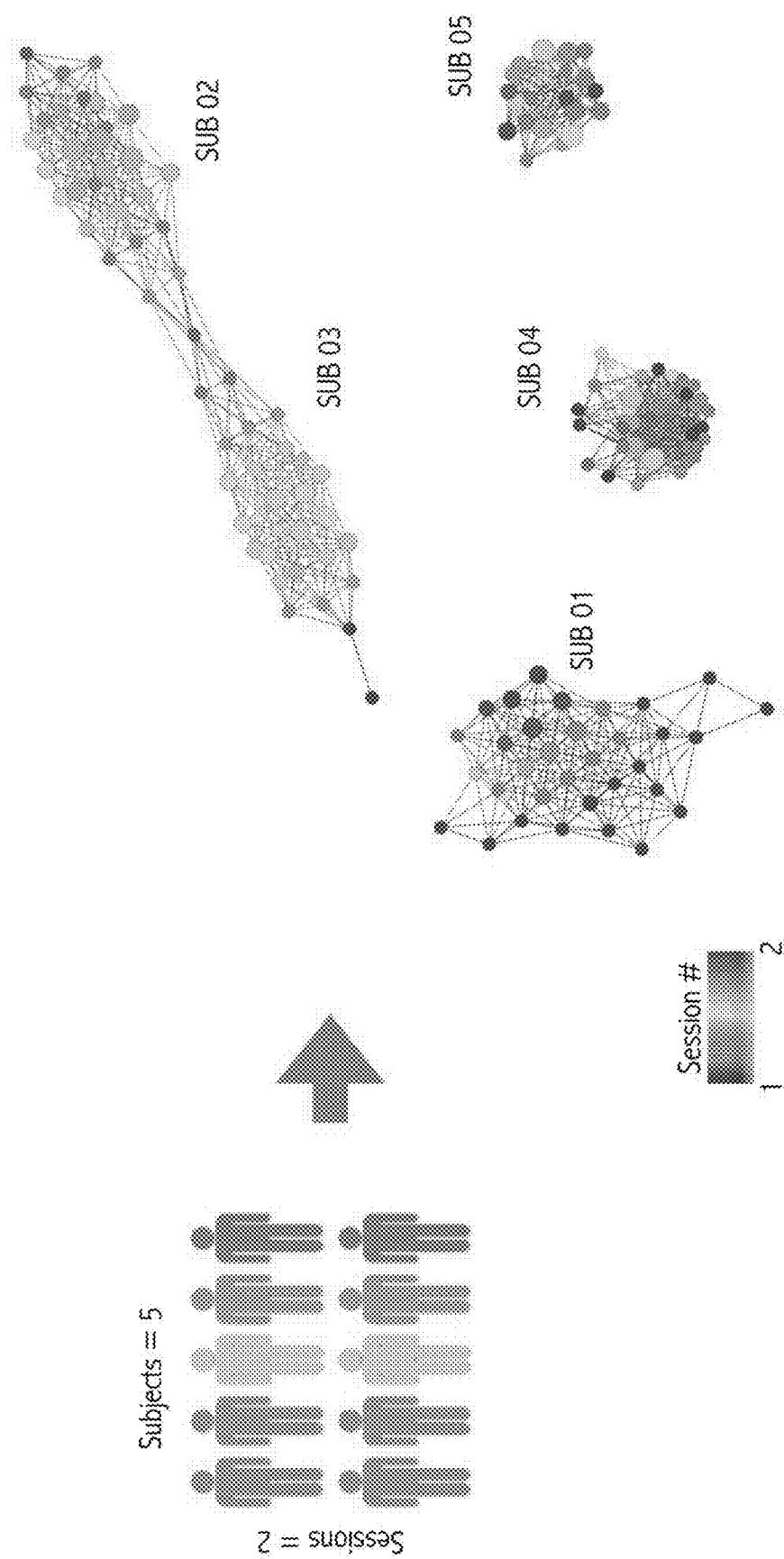
FIG. 4A illustrates the neuronal fingerprints of five individuals in accordance with an embodiment of the invention.

Furthermore, in numerous embodiments, shape graphs are unique to individuals. As such, they can be used to "fingerprint" an individual based on their neuronal circuitry. In many embodiments, experimentally, the same individuals who provide different sets of functional brain imaging data at different times result in having highly correlated shape graphs. Turning now to FIG. 4A, highly correlated shape graphs for 5 individuals over two sessions are illustrated in accordance with an embodiment of the invention. FIG. 4A is produced by putting all of the available data for all 5 individuals into the same instance of a shape graph generation process. Notably, most shape graphs remained distinct, and there are 5 clear different networks present. As such, shape graphs can be used to show the unique neuronal circuitry, and therefore unique topographies of individual neuronal activities.

Figure 4B:
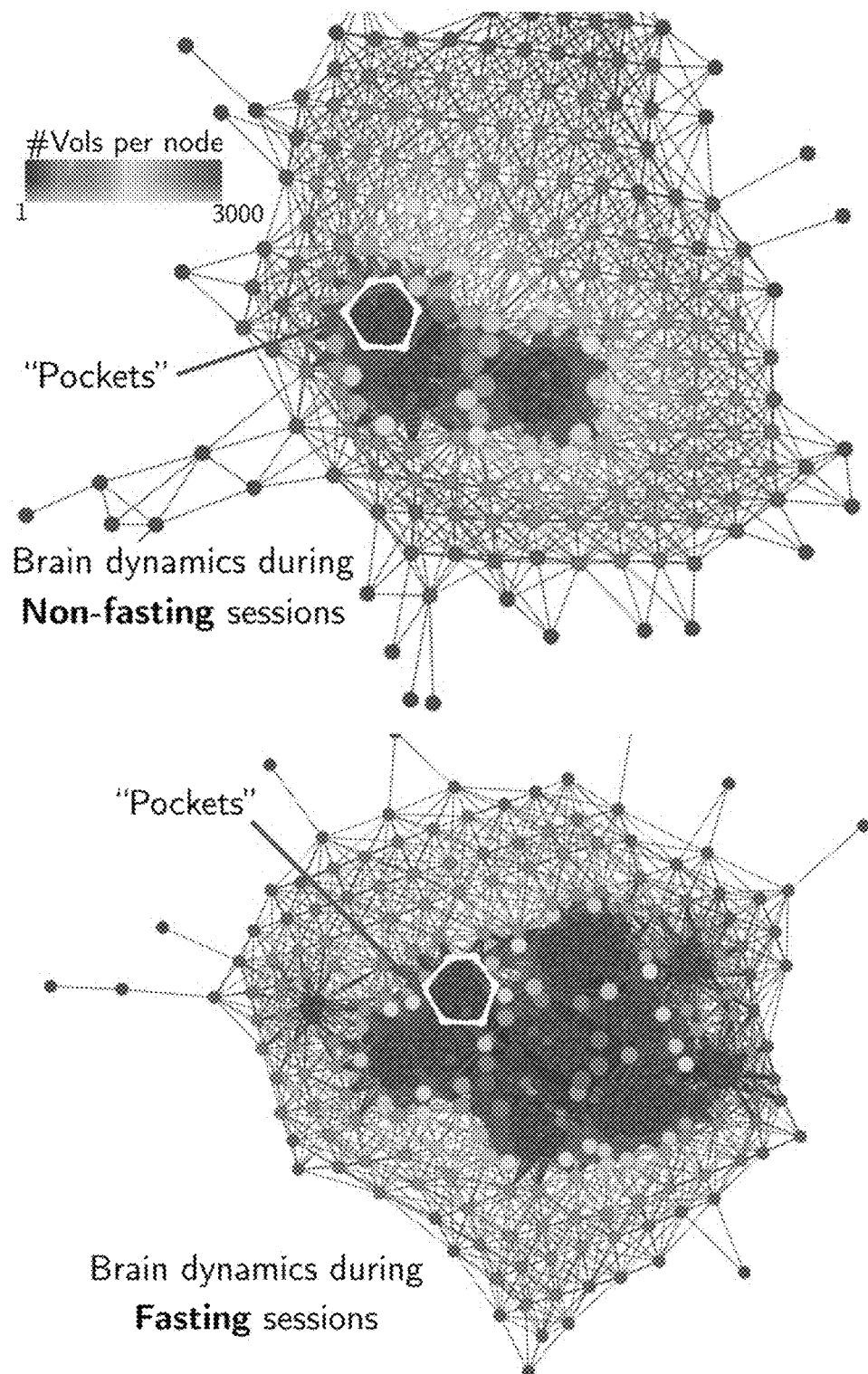
FIG. 4B illustrates the change in an individual's shape graph due to a change in state due to fasting in accordance with an embodiment of the invention.

Further, shape graphs produced by systems and methods described herein are capable of measuring the change in an individual's state. FIG. 4B illustrates two shape graphs, each pertaining to the same individual, but where the data collected for each shape graph was taken during a different state in accordance with an embodiment of the invention. As shown, when an individual was in a non-fasting state shape graph features, for example densely connected sets of nodes ("pockets") appear less frequently, whereas when the individual was in a fasting state, more pockets were present. However, in numerous embodiments of the invention, different shape graph features can be present in differing amounts dependent upon the particular state being measured. Consequently, in a variety of embodiments, shape graphs are sensitive to state changes. Neuronal mapping processes for capturing temporal transitions are discussed below.

Neuronal Mapping Processes for Capturing Temporal Transitions

The ability to measure transitions between tasks can enhance understanding of an individual's neuronal circuitry and cognitive organization. As noted above, shape graphs can illuminate particular neuronal circuitry used for particular tasks. The ability to determine transition between circuits is useful not only for diagnostic purposes (e.g., locating ineffective circuits), but can also shed light on what an individual is doing mentally.

Figure 5A:
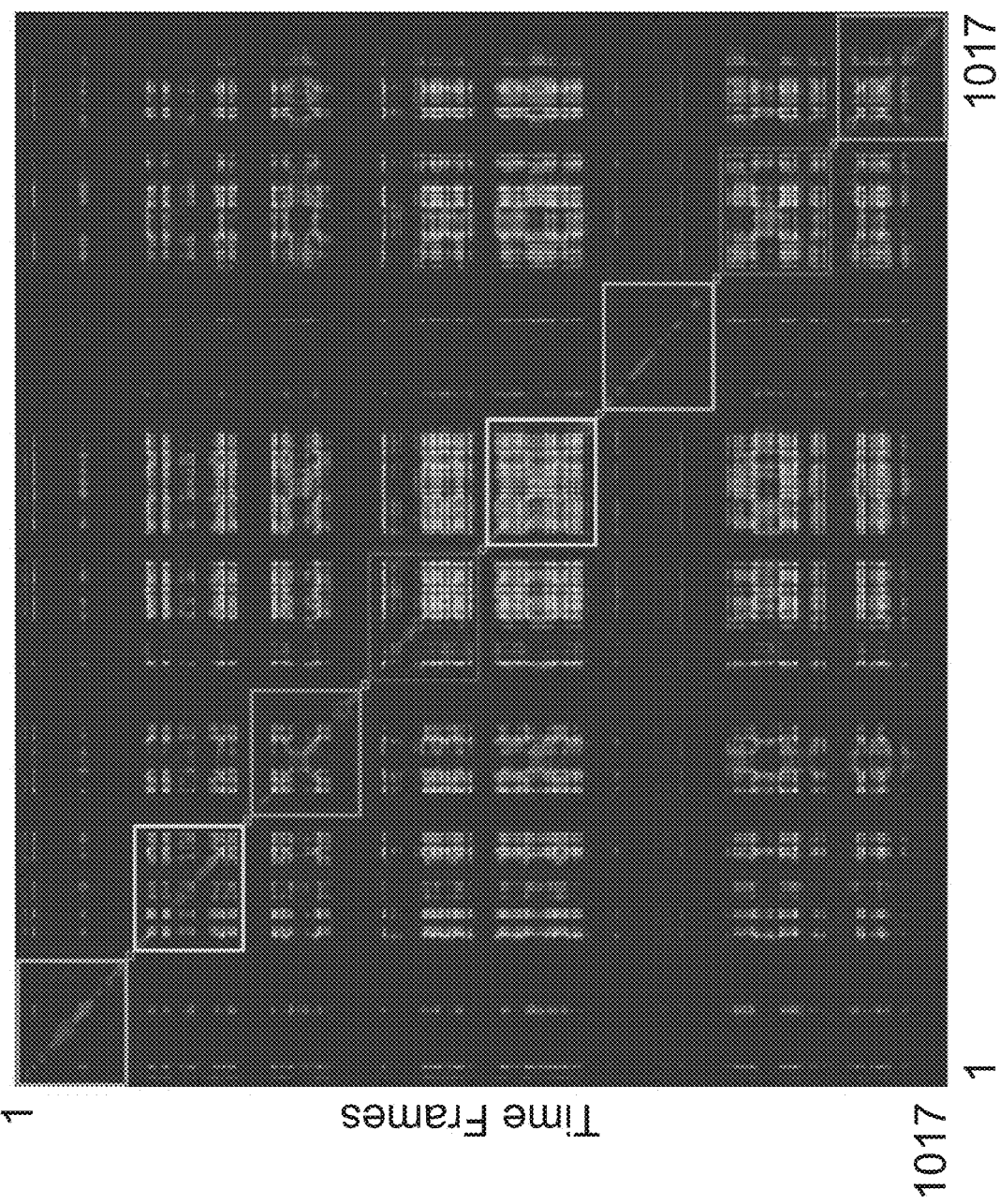
FIG. 5A illustrates a temporal connectivity matrix (TCM) in accordance with an embodiment of the invention.
Figure 5B:
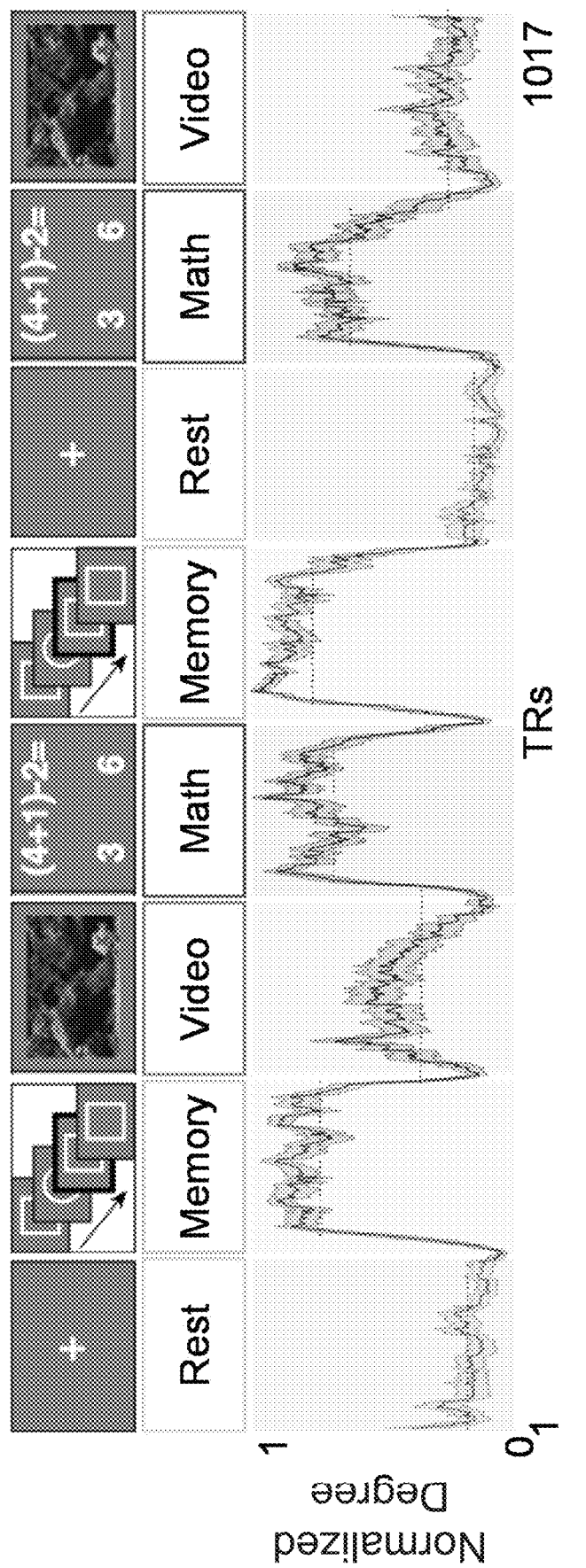
FIG. 5B illustrates the degree of TCM nodes (or TRs) can capture the transition between tasks in accordance with an embodiment of the invention.

To estimate these transitions, shape graphs can be converted to an adjacency matrix in the temporal domain (i.e., a temporal connectivity matrix (TCM)). It is important to note that a TCM is representing similarity (or "connectivity") in time and not in space (like the standard functional connectivity matrices that represent brain region by region connectivity). Here, the time frames can be considered "connected" if they share a node in the shape graph or if the nodes containing these time frames are connected by an edge in the shape graph. Turning now to FIG. 5A, a TCM in accordance with an embodiment of the invention is illustrated. For this particular participant, the TCM is modularly organized, with densely connected frames within each task block and across blocks of the same task. Associated tasks and the corresponding degree of TCM nodes (or TRs) that can capture the transition between tasks in accordance with an embodiment of the invention are illustrated in FIG. 5B. Each task corresponds to one of the squares overlaid in FIG. 5A, descending from left to right. The average degree across all multiple participants is represented as the solid-line, and the shaded region shows the standard error around the mean.

By directly estimating the degree (or the total number of connections) at each time frame in the TCM, the transitions between (and putatively within) task types at the level of a few time frames can be captured. Inherently, a higher degree at any time frame implies greater similarity of that frame with other frames. Thus, during the task blocks, other than resting state block, the evoked activity associated with the stimuli/task can cause the time frames to be highly coherent or similar within each block and across the repetition of the same task (and hence more connected in the TCM), thereby leading to a higher degree value. During the resting state blocks (as well as during between-task instruction periods) the brain activation patterns were driven by intrinsic (and not evoked) activity, which would lead to less coherent or dissimilar patterns and hence a lower degree value. Thus, a task-switch from an evoked task to an instruction period or vice versa can lead to a change in degree values at the level of a few time frames. Using a standard change point detection algorithm, it is possible to retrieve transitions in the mean normalized degree, corresponding to task blocks. Indeed, can capture both the onset and offset of tasks within a matter of a few time frames. Metrics derived from TCMs can be used for clinical diagnostics, such as, but not limited to, diagnosing conditions where low performance for certain tasks is a known behavioral indicator, or where lack of dynamical transitions could be an indication of repetitive/ruminative behavior, or where inattention is a known behavioral indicator, or any other condition where time to perform and/or focus is useful for diagnostics.

While the above processes are discussed with reference to functional imaging with associated tasks, neuronal mapping processes can be performed using resting state functional brain imaging data, i.e. where no tasks are performed and the subject is instructed to let their mind wander. Indeed, shape graphs generated from resting state functional brain imaging data can be used to capture intrinsic dynamics in a patient's brain. For example, in many embodiments, a Markov chain can be generated from a shape graph. In numerous embodiments, the Markov chain is a discreet-time finite-state Markov chain. The Markov chain can be represented as a graph, with nodes as states and directed edges denoting transition probabilities between states. The states can be defined as a set of quasi-stationary whole-brain configuration maps. In numerous embodiments, lower degree of a MC graph suggests high repeatability of states. In this way, the neuronal circuitry of the default mode can be mapped.

Furthermore, in numerous embodiments, shape graphs and/or markov chain graphs can be overlaid onto and/or generated by virtual brain simulations, for example, The Virtual Brain, by The Virtual Brain Initiative (https// www.thevirtualbrain.org). In many embodiments, a shape graph generated from a patient is utilized to parameterize a virtual brain simulation in such a way that the virtual brain attempts to simulate the patient's brain. Experiments can be run on the simulation to investigate possible treatments, and new shape graphs can be generated from the simulation post virtual treatment to determine the efficacy of different treatments prior to application to the patient. In various embodiments, the treatments derived can be transcranial magnetic stimulation treatments, implant based treatments, drug based treatments, and/or any other treatment regimen as appropriate to requirements of a given application of an embodiment of the invention. Systems for performing neuronal mapping processes are discussed below.

Neuronal Mapping Systems

Neuronal mapping systems can be used to acquire functional brain imaging data and perform neuronal mapping processes. In numerous embodiments, neuronal mapping systems are constructed of multiple computing systems. In a variety of embodiments, neuronal mapping systems are implemented on a single computing system. Neuronal mapping systems can process a wide variety of image data, however certain specific embodiments can be utilized for processing fMRI image data.

Figure 6:
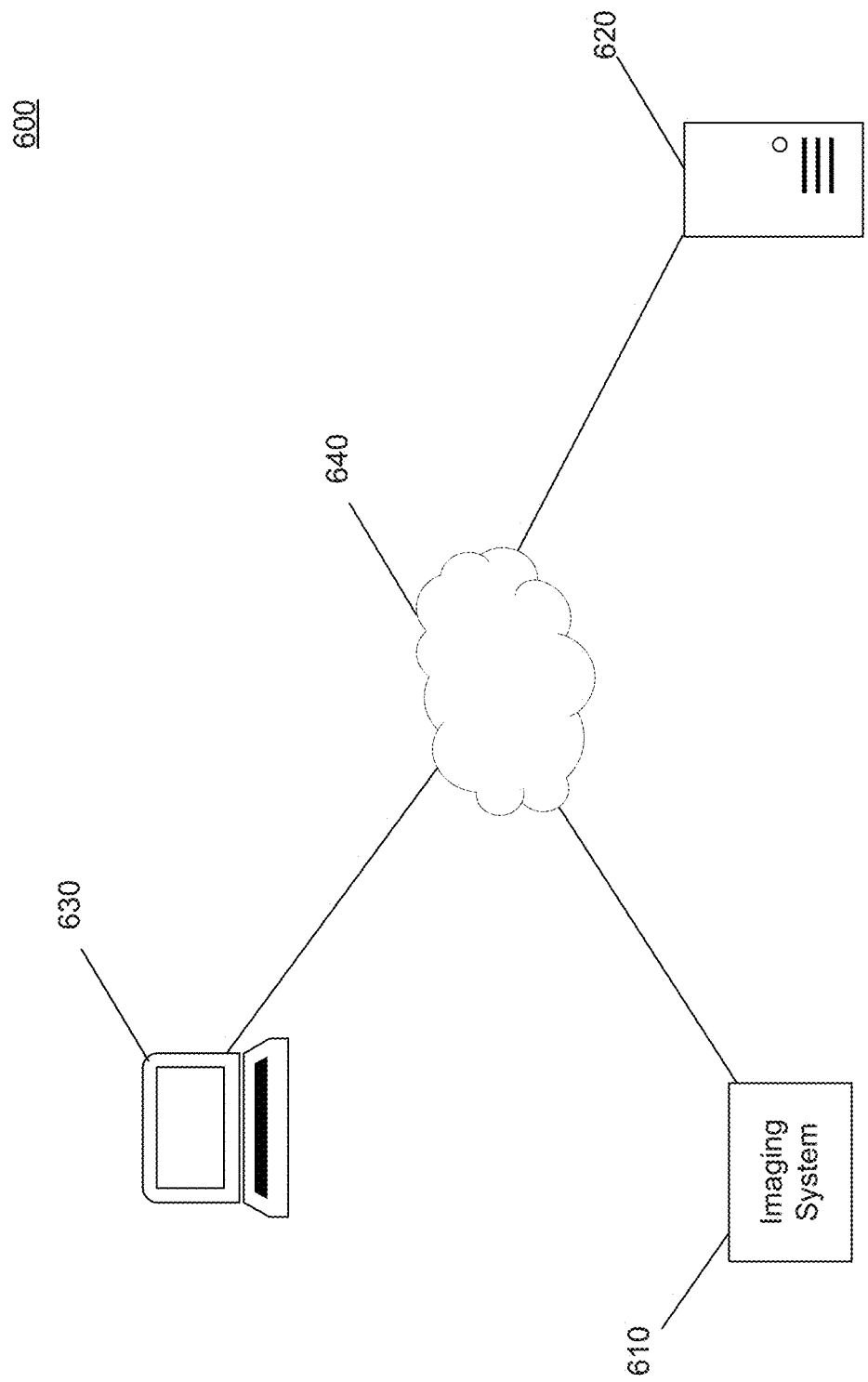
FIG. 6 illustrates a neuronal circuitry mapping system in accordance with an embodiment of the invention.

Turning now to FIG. 6, a system diagram of an image processing system in accordance with an embodiment of the invention is illustrated. Image processing system 600 has at least one imaging system 610. Imaging system 610 is connected to neuronal mapping computing system 620 and interface device 630 via network 640. In many embodiments, the imaging system is an fMRI imaging device. However, the imaging system can be any device capable of capturing an image as appropriate to the requirements of a given application.

The imaging system can include various peripheral devices, including terminals, display devices, and other interface devices, for example those utilized for performing task based tests. The neuronal mapping computing system can be implemented on a personal computer, a server computer system, or any other computing device as appropriate to the requirements of a given application. The interface device can be a personal computer, a tablet computer, a smartphone, a monitor, and/or any other device as appropriate to the requirements of a given application.

Neuronal mapping computer systems can include a processor, memory, and/or at least one storage system containing an image processing application that includes machine readable instructions that configures the computer to process functional brain imaging data in accordance with methods described below. In some embodiments, the image processing interface device and the image processing server system are on the same platform. The network can be, but is not limited to, the Internet, a local area network, a wireless local area network, wide area network, a software defined network, and/or any other type or combination of types of network as appropriate to the requirements of a given application.

Devices described above can communicate via the network via communications ports. In many embodiments, data is transferred between one or more devices via the network. In a variety of embodiments, data transfer between one or more devices is achieved using physical media transfer, such as a flash drive, compact discs, or any other physical storage media as appropriate to the requirements of a given application.

Functional brain imaging data obtained via the imaging system and describing the captured image can be sent via the network to the neuronal mapping computer system for analysis. In some embodiments, functional brain imaging data is also sent to the image processing interface device. In numerous embodiments, the neuronal mapping computer system processes received image data and outputs results to the interface device. In a variety of embodiments, some processing is done by the interface device.

Processed data and/or any other output of the system can be provided to the user by a user interface device. In many embodiments, user interface devices provide graphical user interfaces which enable a user to access data. In many embodiments, the user interface device is connected to the network. Neuronal mapping computer systems are described in further detail below.

Neuronal Mapping Computer Systems

Figure 7:
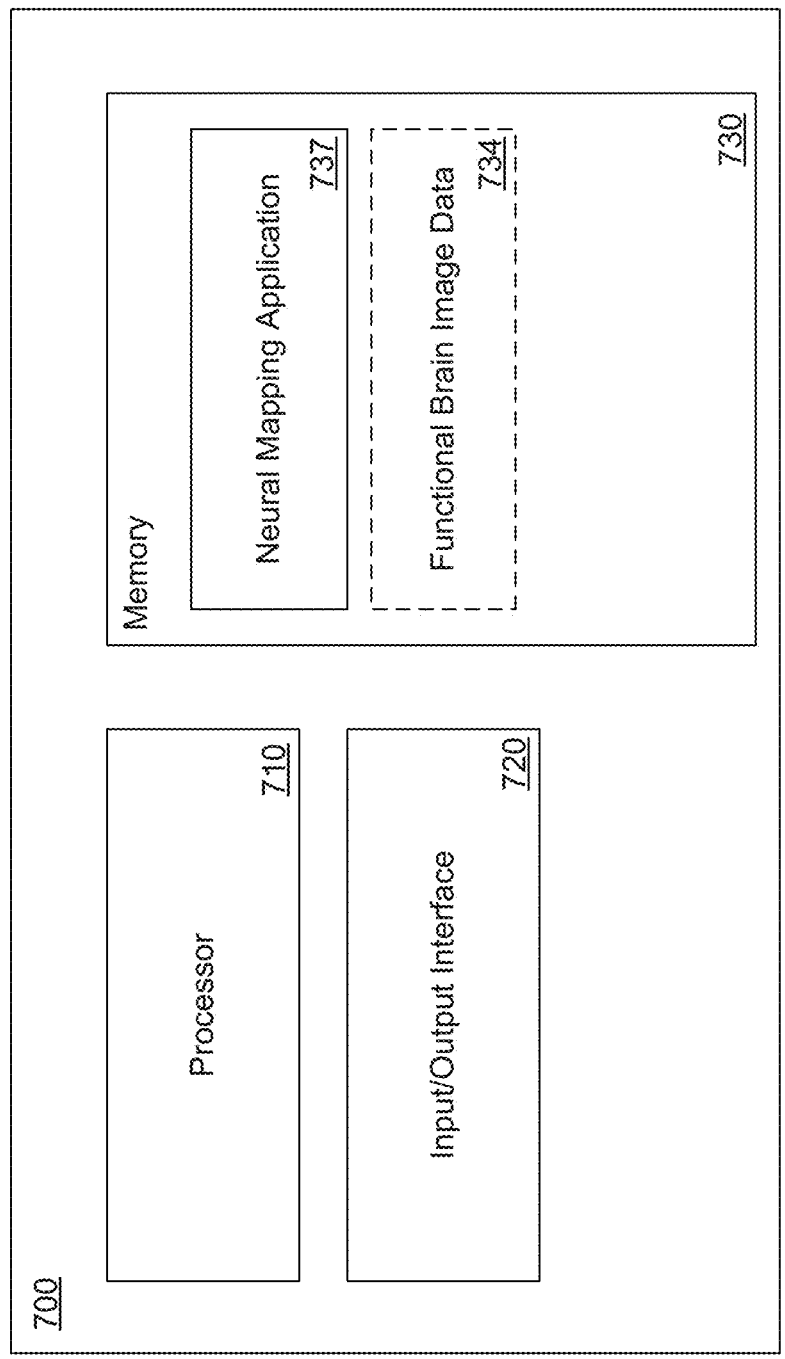
FIG. 7 illustrates a neuronal circuitry mapping computer system in accordance with an embodiment of the invention.

Neuronal mapping computer systems in accordance with embodiments of the invention can perform neuronal mapping processes similar to those described above. A conceptual illustration of a neuronal mapping computer system in accordance with an embodiment of the invention is shown in FIG. 7 neuronal mapping computer system 700 includes a processor 710 in communication with a communications interface 720 and a memory 730. In numerous embodiments, neuronal mapping computer systems comprise multiple processors, multiple memories, and/or multiple communications interfaces. In a variety of embodiments, components of neuronal mapping computer systems are distributed across multiple hardware platforms.

Processor 710 can be any type of computational processing unit, including, but not limited to, microprocessors, central processing units, graphical processing units, parallel processing engines, or any other type of processor as appropriate to the requirements of specific applications of embodiments of the invention. Communications interface 720 can be utilized to transmit and receive data from other neuronal mapping computer systems, imaging systems, interface devices, and/or any other 3$^{rd}$ party device as appropriate to the requirements of a given application of the invention. Communications interfaces can include multiple ports and/or communications technologies in order to communication with various devices as appropriate to the requirements of specific applications of embodiments of the invention.

Memory 730 can be implemented using any combination of volatile and/or non-volatile memory, including, but not limited to, random access memory, read-only memory, hard disk drives, solid-state drives, flash memory, or any other memory format as appropriate to the requirements of specific applications of embodiments of the invention. In numerous embodiments, the memory 730 stores a variety of data, including, but not limited to, a neuronal mapping application 732 and functional brain imaging data 734. In many embodiments, the neuronal mapping application and/or the functional brain imaging data are received via the communications interface. Processor 710 can be directed by the neuronal mapping application to perform a variety of neuronal mapping processes, including, but not limited to, generating shape graphs.

Although specific architectures for neuronal mapping computer systems in accordance with embodiments of the invention are conceptually illustrated in FIG. 7, any of a variety of architectures can also be utilized. Furthermore, neuronal mapping computer systems can be implemented on multiple servers within at least one server system. For example, neuronal mapping computer systems can be implemented on various remote "cloud" server systems as appropriate to the requirements of specific applications of embodiments of the invention. However, one of ordinary skill in the art would appreciate that a "server system" can be implemented on any appropriate computing device, including, but not limited to, a personal computer and/or a computing device incorporated into a medical device. In numerous embodiments, neuronal mapping computer systems are implemented as part of an integrated imaging system.

In numerous embodiments, neuronal mapping systems can be implemented in "at home" style devices which are usable by consumers. For example, EEGs can be utilized for recording functional brain imaging data, and generation of shape graphs and/or analysis can be done using consumer grade computing devices.

Although specific systems and methods of mapping neuronal circuitry and their applications are discussed above, many mapping methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for generating and using a neuronal shape graph, comprising:

obtaining functional brain imaging data from an imaging device, where the functional brain imaging data comprises a time-series of voxels describing neuronal activation over time in a patient's brain;

lowering the dimensionality of the functional brain imaging data to a set of points, where each point represents a brain state of the patient at a particular time in the time-series;

binning the points into a plurality of bins;

clustering the binned points;

generating a shape graph of the patient's brain state dynamics from the clustered points, where nodes in the shape graph represent a brain state and edges between the nodes represent transitions between brain states;

identifying at least one topological feature of the shape graph of the patient's brain state dynamics associated with a pathophysiology of a mental disorder; and supporting a diagnosis of the mental disorder for the patient.

2. The method for generating a neuronal shape graph of claim 1, wherein lowering the dimensionality of the functional brain imaging data is performed using a neighborhood lens function.

3. The method for generating a neuronal shape graph of claim 1, wherein binning the points partitions the low dimensional points into overlapping bins.

4. The method for generating a neuronal shape graph of claim 1, wherein clustering the binned points is achieved using single-linkage clustering.

5. The method for generating a neuronal shape graph of claim 1, wherein the imaging device is a functional magnetic resonance imaging machine.

6. The method for generating a neuronal shape graph of claim 1, wherein the functional brain imaging data is resting state functional brain imaging data.

7. The method for generating a neuronal shape graph of claim 6, further comprising generating a Markov chain graph.

8. The method for generating a neuronal shape graph of claim 1, further comprising annotating the nodes in the shape graph with task data.

9. The method for generating a neuronal shape graph of claim 1, further comprising identifying at least one set of core nodes and at least one set of periphery nodes in the shape graph.

10. The method for generating a neuronal shape graph of claim 1, further comprising identifying a community structure within the shape graph.

11. A system for generating and using a neuronal shape graph, comprising:

at least one processor; and at least one memory, comprising a neuronal mapping application, where the neuronal mapping application directs the processor to:

obtain functional brain imaging data from an imaging device, where the functional brain imaging data comprises a time-series of voxels describing neuronal activation over time in a patient's brain;

lower the dimensionality of the functional brain imaging data to a set of points, where each point represents a brain state of the patient at a particular time in the time-series;

bin the points into a plurality of bins;

cluster the binned points;

generate a shape graph of the patient's brain state dynamics from the clustered points, where nodes in the shape graph represent a brain state and edges between the nodes represent transitions between brain states;

identify at least one topological feature of the shape graph of the patient's brain state dynamics associated with a pathophysiology of a mental disorder; and support a diagnosis of the mental disorder for the patient.

12. The system for generating a neuronal shape graph of claim 11, wherein the neuronal mapping application further directs the processor to lower the dimensionality of the functional brain imaging data is performed using a neighborhood lens function.

13. The method for generating a neuronal shape graph of claim 1, wherein the bins are overlapping.

14. The method for generating a neuronal shape graph of claim 1, wherein the neuronal mapping application directs the processor to cluster the binned points using single-linkage clustering.

15. The method for generating a neuronal shape graph of claim 1, wherein the imaging device is a functional magnetic resonance imaging machine.

16. The method for generating a neuronal shape graph of claim 1, wherein the functional brain imaging data is resting state functional brain imaging data.

17. The method for generating a neuronal shape graph of claim 6, wherein the neuronal mapping application further directs the processor to generate a Markov chain graph.

18. The method for generating a neuronal shape graph of claim 1, wherein the neuronal mapping application further directs the processor to annotate the nodes in the shape graph with task data.

19. The method for generating a neuronal shape graph of claim 1, wherein the neuronal mapping application further directs the processor to identify at least one set of core nodes and at least one set of periphery nodes in the shape graph.

20. The method for generating a neuronal shape graph of claim 1, wherein the neuronal mapping application further directs the processor to identify a community structure within the shape graph.

* * * * *